United States Patent
Lee et al.

(10) Patent No.: US 10,723,775 B2
(45) Date of Patent: Jul. 28, 2020

(54) METHOD FOR PURIFYING DARBEPOETIN ALFA

(71) Applicant: CJ Healthcare Corporation, Seoul (KR)

(72) Inventors: Yoon Jung Lee, Yongin-si (KR); Kyung Hwa Kim, Busan (KR); Yoo Hee Yang, Yongin-si (KR); Jung Min Yoo, Seoul (KR); Se Jun Kim, Gwacheon-si (KR); Ji Hyun Moon, Seoul (KR); Hoo Keun Oh, Suwon-si (KR); Dong Eok Lee, Seoul (KR); Won Jeong Lee, Seoul (KR); Jung Rok Lee, Busan (KR); Chung Min Lee, Yongin-si (KR); Eun Young Choi, Seoul (KR); Gyong Sik Ha, Suwon-si (KR)

(73) Assignee: CJ Healthcare Corporation, Seoul (KR)

( * ) Notice: Subject to any disclaimer, the term of this patent is extended or adjusted under 35 U.S.C. 154(b) by 0 days.

(21) Appl. No.: 15/039,569

(22) PCT Filed: Nov. 28, 2014

(86) PCT No.: PCT/KR2014/011527
§ 371 (c)(1),
(2) Date: May 26, 2016

(87) PCT Pub. No.: WO2015/080509
PCT Pub. Date: Jun. 4, 2015

(65) Prior Publication Data
US 2017/0022257 A1    Jan. 26, 2017

(30) Foreign Application Priority Data

Nov. 29, 2013 (KR) .................. 10-2013-0148026

(51) Int. Cl.
C07K 1/18 (2006.01)
C07K 1/34 (2006.01)
C07K 14/505 (2006.01)

(52) U.S. Cl.
CPC .............. C07K 14/505 (2013.01); C07K 1/18 (2013.01)

(58) Field of Classification Search
None
See application file for complete search history.

(56) References Cited

U.S. PATENT DOCUMENTS

2008/0314750 A1* 12/2008 Hagner-McWhirter ...................... B01D 15/168
204/459
2012/0149878 A1    6/2012 Gillespie et al.
2016/0347788 A1* 12/2016 Bolton ..................... C07K 1/22

FOREIGN PATENT DOCUMENTS

| KR | 10-2009-0064377 A | 6/2009 |
|---|---|---|
| KR | 10-2013-0042107 A | 4/2013 |
| WO | WO 95/05465 A1 | 8/1994 |
| WO | WO 00/27869 A1 | 5/2000 |
| WO | WO 01/76640 A2 | 10/2001 |
| WO | WO 03/045996 A1 | 6/2003 |
| WO | WO 2010/008823 A2 | 1/2010 |
| WO | WO 2011/024024 A1 | 3/2011 |
| WO | WO 2011/156369 A2 * | 12/2011 |
| WO | WO 2013/002330 A1 | 3/2013 |
| WO | WO 2013/058485 A1 | 4/2013 |

OTHER PUBLICATIONS

Caldini et al., "Epoetin Alpha, Epoetin Beta and Darbepoetin Alfa: Two-Dimensional Gel Electrophoresis Isoforms Characterization and Mass Spectrometry Analysis," *Proteomics* (2003), 3:937-931, Wiley-VCH Verlag GmbH & Col. KGaA, Weinheim, Germany.
Egrie and Browne, "Development and Characterization of Novel Erythropoiesis Stimulating Protein (NESP)," *Br. J. Cancer Suppl.* (2001), 84:3-10, Cancer Research Campaign.
Ejima et al., "Improved Column Chromatography Performance Using Arginine," *American Laboratory* (2007).
Morkeberg et al., "Detection of Darbepoetin Alfa Misuse in Urine and Blood: A Preliminary Investigation," *Med. Sci. Sports Exerc.* (2007), 39(10):1742-1747, American College of Sports Medicine.
Pedrazzoli et al., "Darbepoetin Alpha Coming of Age," *Anticancer Res.* (2007) 27:4419-4424.
European Office Action dated Jul. 24, 2018, regarding EP 14 865 782.8.

* cited by examiner

*Primary Examiner* — Elizabeth C. Kemmerer
*Assistant Examiner* — Regina M DeBerry
(74) *Attorney, Agent, or Firm* — Morgan, Lewis & Bockius LLP

(57) ABSTRACT

The present invention relates to a method for purifying darbepoetin alfa by selectively separating only a structural isoform having a high content of sialic acid from a mixture of structural isoforms of darbepoetin alfa having various contents of sialic acid. Since the method of the present invention is a novel method for purifying darbepoetin alfa which can be conveniently and simply produced, it is possible to remarkably increase productivity due to process efficiency improvement, as well as to yield high purity darbepoetin alfa when mass-producing darbepoetin alfa according to the present invention.

14 Claims, 6 Drawing Sheets

1. loading solution for anion exchange chromatography
2. 1st washing solution for anion exchange chromatography
3. 2nd washing solution for anion exchange chromatography (Gly/HCl buffer solution containing L-arginine)
4. marker
5. eluate from anion exchange chromatography use of washing solution containing L-arginine in a sodium acetate buffer solution
1. eluate from anion exchange chromatography
2. marker
3. loading solution for anion exchange chromatography use of glycine-HCl buffer solution not containing arginine as a washing solution 1. eluate from anion exchange resin chromatography
2. Marker 1. fraction 1
2. fraction 2
3. fraction 3
4. fraction 4
5. fraction 5
6. MARKER

METHOD FOR PURIFYING DARBEPOETIN ALFA

CROSS-REFERENCE TO RELATED APPLICATIONS

This application is a 35 USC § 371 National Stage application of International Application No. PCT/KR2014/011527 filed Nov. 28, 2014, now pending; which claims the benefit under 35 USC § 119(a) to Korea Patent Application Serial No. 10-2013-0148026 filed Nov. 29, 2013. The disclosure of each of the prior applications is considered part of and is incorporated by reference in the disclosure of this application.

BACKGROUND OF THE INVENTION

1. Field of the Invention

The present invention relates to a method for purifying darbepoetin alfa by selectively separating only a structural isoform having a high content of sialic acid from a mixture of structural isoforms of darbepoetin alfa having various contents of sialic acid.

2. Description of the Related Art

Darbepoetin alfa (NESP) is an analogue of erythropoietin (EPO), which has five substitutes in the amino acid sequence of the erythropoietin molecule, providing two additional N-glycosylated chains (International Publication No. WO 2001076640). Although darbepoetin alfa differs from EPO in terms of biochemical characteristics such as molecular weight, isoelectric point, etc., it is also an erythropoiesis-stimulating protein like EPO.

Darbepoetin alfa is known to have a serum half-life which is about three times longer than that of erythropoietin in mice, rats, dogs, humans, etc., due to its high sialic acid content (Pedrazzoli P, Cinieri S, Lorusso V, Gamucci T, Secondino S, Silvestris N 2007 November-December, 27(6C), 4419-24; Anticancer Res.), and thus its in vivo decomposition is inhibited, thereby affording a higher biological activity than that of EPO in its natural state.

Darbepoetin alfa, due to the difference in sialic acid content by glycosylation, maximally has 22 different types of structural isoforms, and the higher the sialic acid content is, the lower the isoelectric point and the higher therapeutic value are. Accordingly, the selective separation and purification of only the structural isoforms with a high sialic acid content is very important in the therapeutic field using darbepoetin alfa.

Examples of the conventional method for purifying EPO and EPO analogues include anion exchange and cation exchange chromatographies, hydrophobic-interaction chromatography, size-exclusion chromatography, etc. Specifically, International Publication No. WO 2010/027869 discloses a method for purifying EPO by sequentially applying hydrophobic-interaction, anion exchange, cation exchange, and size-exclusion chromatographies. International Publication No. WO 2003/045996 discloses a method for purifying recombinant human EPO by performing a reverse phase chromatography, anion exchange chromatography, and size-exclusion chromatography.

In particular, as methods for purifying darbepoetin alfa, International Publication No. WO 1995/005465 discloses a method for applying anion exchange resin and C4 resin, and International Publication No. WO 2010/008823 suggests a flow-through mode for the purification of darbepoetin alfa having a high sialic acid content with an isoelectric point of 4.5 or less, in which the target protein is not bound to the column of the cation exchange resin but is flowed out in the chromatography treatment solution. However, these methods require extremely high cost and much time due to their use of various steps of resins, and are thus not suitable for large-scale production.

Meanwhile, Korean Patent Application Publication No. 10-2013-0042107 discloses a method which is more simplified than the above four-step process, by adopting a three-step process which sequentially applies anion, hydroxyapatite, anion exchange chromatography, and performing adsorption and washing under a particular pH condition when a secondary anion exchange resin chromatography is applied, for selective separation of isoforms having low isoelectric points. In particular, for obtaining isoforms with low isoelectric points, darbepoetin alfa is bound to the column at a pH ranging from 4.0 to 5.0 followed by washing with a buffer solution having a pH ranging from 2.0 to 2.4.

The above method may be advantageous in terms of time and cost required in large-scale production because the process is a bit simplified compared with the conventional processes, however, for the embodiment of the low pH condition (pH ranging from 2.2 to 2.4) as suggested in the above published patent application, it is necessary that a toxic, acidic solution such as HCl be used in a large amount, and thus this method is not desirable. Additionally, since the reactions of isoforms at a given pH condition are not constant when the amount to be treated by the column is increased at the time of scale-up, the possibility of reproducibility in large-scale production is low when isoforms with a desirable range of isoelectric points are to be obtained by controlling pH conditions of a buffer solution.

That is, since the conventional method of purifying darbepoetin alfa requires a complex process using chromatography consisting of various steps of resins, it requires an extremely high cost and much time, and when the purifying is performed using a process which is simplified compared with the conventional process, it is necessary that the conditions such as pH be precisely controlled to compensate for the purification effect that may be reduced, but it becomes more difficult to control the conditions as the production scale becomes larger.

As such, there is an increasing demand for an improved method of purifying darbepoetin alfa which, being more simplified than the conventional methods and having more easily controllable process conditions, can stably reproduce successful process conditions while reducing cost and time when the method is applied to large-scale production.

SUMMARY OF THE INVENTION

The present inventors endeavored to develop a method for purifying darbepoetin alfa with improved convenience and simplicity compared with the conventional processes, and as a result, have surprisingly discovered that a simple method of using only anions and arginine can separate darbepoetin alfa with a high sialic acid content within a short period of time, thereby completing the present invention.

Accordingly, an object of the present invention is to provide a method for purifying darbepoetin alfa having a high content of sialic acid from a mixture of structural isoforms of darbepoetin alfa having various contents of sialic acid.

ADVANTAGEOUS EFFECTS OF THE INVENTION

The method of the present invention is a novel method for purifying darbepoetin alfa which can be conveniently and simply produced, and it is possible to remarkably increase productivity due to the improvement in process efficiency as well as to yield high purity darbepoetin alfa at the time of large-scale production according to the present invention.

DETAILED DESCRIPTION OF THE PREFERRED EMBODIMENTS

Figure 1A:
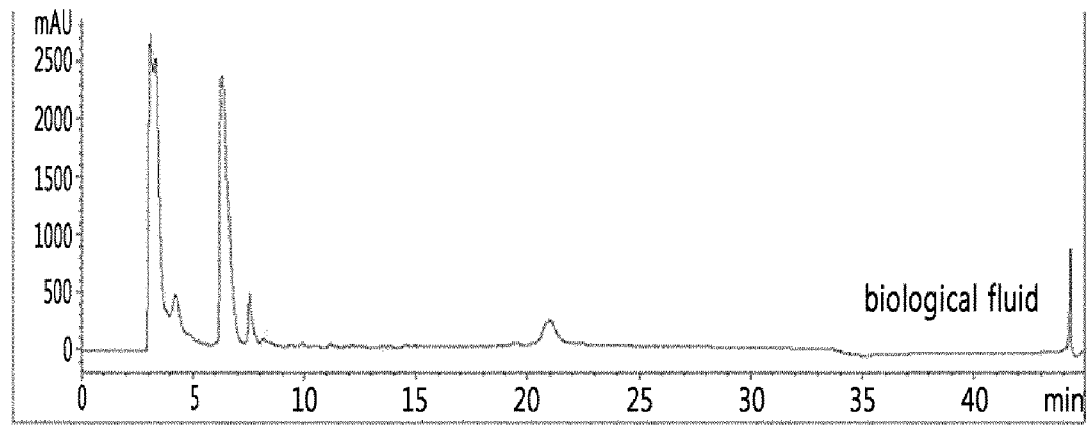
FIG. 1A, FIG. 1B and FIG. 1C show the purities of eluates of darbepoetin alfa, which were obtained by purification by anion exchange-hydroxyapatite resin chromatography, analyzed by C4 HPLC.

In order to achieve the above object, in an aspect, the present invention provides a method for purifying darbepoetin alfa from a mixture of structural isoforms of darbepoetin alfa having various contents of sialic acid.

Specifically, for selective separation of structural isoforms having a high content of sialic acid from a mixture of structural isoforms of darbepoetin alfa, the present invention provides a method for purifying darbepoetin alfa by anion exchange chromatography including washing with a washing buffer solution containing arginine.

Preferably, the method for purifying darbepoetin alfa according to the present invention includes performing at least one anion exchange chromatography, wherein the performance of the anion exchange chromatography includes binding a mixture of structural isoforms of darbepoetin alfa to the anion exchange resin, washing the resin with a buffer solution containing arginine, and eluting the darbepoetin alfa bound to the chromatography column from the column.

In another exemplary embodiment, the present invention provides a method for purifying darbepoetin alfa including the steps of: (a) binding darbepoetin alfa to an anion exchange chromatography column by loading a mixture containing darbepoetin alfa having various contents of sialic acid into the anion exchange chromatography column; (b) washing the chromatography column with a washing buffer solution containing arginine; and (c) eluting the darbepoetin alfa, which remains bound to the chromatography column, from the column.

In an exemplary embodiment, the present invention provides a method for purifying darbepoetin alfa including the steps of: (a) eluting a darbepoetin alfa-containing fraction by applying a biological fluid comprising darbepoetin alfa to anion exchange chromatography; (b) eluting a darbepoetin alfa-containing fraction by applying the eluate produced in step (a) to hydroxyapatite resin chromatography; (c) binding darbepoetin alfa to an anion exchange chromatography column by loading the eluate produced in step (b) into the anion exchange chromatography column; (d) washing the column treated in step (c) with a washing buffer solution containing arginine; and (e) eluting the darbepoetin alfa, which remains bound to the chromatography column by washing in step (d), from the column.

The present invention is described in greater detail herein below.

As used herein, the term "darbepoetin alfa", being in a recombinant form of erythropoietin (EPO), which is a glycoprotein, refers to a glycoprotein which has five substitutions in the amino acid sequence of the erythropoietin molecule, thereby providing two additional N-glycosylated chains. Darbepoetin alfa is distinguished from erythropoietin in biochemical characteristics such as molecular weight, isoelectric point, etc. Darbepoetin alfa induces erythropoiesis and thus can be used as a therapeutic agent for renal failure or anemia associated with chemical treatment of cancer. Due to the glycans added therein, darbepoetin alfa has a serum half-life which is about three times longer than that of erythropoietin, and can be present in various isoforms according to the sialic acid content. The structural isoforms of darbepoetin alfa with high contents of glycans and sialic acid have low isoelectric points, and these structural isoforms have high biological activities in vivo. Accordingly, the selective separation and purification of only the structural isoforms with high contents of glycans and sialic acid is very important in therapeutic protein agents using darbepoetin alfa, however, the conventional purification methods have problems in that they require extremely high cost and much time due to the use of resins in several steps. In this regard, the present inventors have developed a method for purifying darbepoetin alfa with high glycosylation only by a simplified process within a short period of time.

As Darbepoetin alfa has higher glycosylation level than that of EPO, the sialic acid content per 1 mole of darbepoetin alfa is higher than that of EPO, which has a maximum 13 moles per 1 mole of EPO, and the maximum theoretical value of sialic acid content per 1 mole of darbepoetin alfa is known to be 22 moles (Development and characterization of novel erythropoiesis stimulating protein (NESP), British Journal of Cancer (2001) 84 (Supplement 1), 3-10).

In particular, the darbepoetin alfa, being separated and purified according to the purification method of the present invention, has high contents of glycans and sialic acid, preferably is one having structural isoforms with a low isoelectric point ranging from pI 2.0 to pI 4.0, and more preferably with an isoelectric point of 3.5 or less.

As used herein, the term "biological fluid" refers to a culture containing cells, cell constituents, or cell products, or derivatives thereof, and although it is not limited thereto, may include cell cultures, cell culture supernatants, cell lysates, cell extracts, tissue extracts, blood, blood sera, milk, urines, fractions thereof, etc. In the purification of the present invention, the biological fluid to be used may be in various types. Preferably, the biological fluid may be a yeast, a plant, or an animal cell culture, more preferably, an animal cell culture of a transgenic animal, into which a nucleotide sequence encoding darbepoetin alfa is transfected by genetic recombination, and even more preferably, an animal cell culture, wherein the animal cell is from Chinese hamster ovary (CHO). When the animal cell culture is used, as known in the art, it is more preferable that the supernatant obtained by centrifugation of the culture is used.

Preferably, the biological fluid of the present invention may be obtained by using an ultrafiltration/diafiltration method. The ultrafiltration/diafiltration method can not only remove low molecular weight materials of 10,000 molecular weight cut off (MWCO) (e.g., surfactants, dyeing agents, small peptides, sugar components, etc.) in a culture, but can also improve the column adsorption efficiency by subsequently replacing the buffer solution with a chromatography equilibrium buffer solution.

In an exemplary embodiment of the present invention, CHO cells transfected with a vector containing darbepoetin alfa were cultured, and the supernatant of the culture was diafiltrated via ultrafiltration (using a 10 mM sodium phosphate buffer solution) and used as a biological fluid.

As used herein, the term "anion exchange chromatography" refers to a process that separates molecules based on their charges by binding negatively charged (or acidic) molecules to a positively charged support, and homologous molecules (acidic, basic, neutral) can be easily separated by this technique. Both a strong anion exchange resin and a weak anion exchange resin may be used in the present invention without limitation, for example, Sephadex™, Sepharose™, SOURCE™, Mono Q™, and Mini Q™ (GE healthcare), and resins in which the functional group is a quaternary amine (Q), diethylaminoethyl (DEAE), or quaternary aminoethyl (QAE), may be used, although they are not limited thereto. Preferably, the functional group may be Q or DEAE, and most preferably, Q-Sepharose™, which is a strong anion exchange resin.

Anion exchange chromatography may be performed by column chromatography. Additionally, the anion exchange resin used in anion exchange chromatography of the present invention may be equilibrated using an aqueous buffer solution before adsorbing the culture thereto, and examples of the buffer solution may include Tris-HCl, sodium phosphate buffer solution, etc.

Additionally, the anion exchange resin used in anion exchange chromatography of the present invention may be equilibrated using an aqueous buffer solution before adsorbing the culture thereto.

The stationary phase of the adsorption chromatography used in the present invention may include silica, alumina, magnesium oxide, and hydroxyapatite, and most preferably hydroxyapatite. In particular, hydroxyapatite is known to be widely used for conventional removal of nucleic acids such as DNA.

After removal of the biological impurities from the fraction of darbepoetin alfa, the darbepoetin alfa fraction including structural isoforms of various sialic acid contents is subjected to anion exchange chromatography, thereby selectively separating darbepoetin alfa with a high sialic acid content. In the purification method of the present invention, washing with a washing buffer solution containing arginine may be to wash structural isoforms of darbepoetin alfa having isoelectric points higher than the desired isoelectric point, for the purpose of obtaining structural isoforms of darbepoetin alfa having the desired isoelectric point.

For the purpose of the present invention, the anion exchange chromatography column is washed using a washing solution containing arginine.

In the present invention, the arginine-containing washing buffer solution may preferably have a pH ranging from 3.0 to 5.0, and may further include at least one selected from the group consisting of NaCl and urea. In particular, the washing buffer solution may contain NaCl at a concentration ranging from 5 mM to 90 mM, and may contain urea at a concentration ranging from 3 M to 8 M.

Preferably, the purification method of the present invention may further include washing with a washing buffer solution with or without arginine, before or after washing the chromatography column with a washing buffer solution containing arginine, after loading a mixture comprising darbepoetin alfa having various contents of sialic acid into an anion exchange chromatography column and binding darbepoetin alfa to the column, and more preferably, may further include a primary washing of the chromatography column with a washing buffer solution having a pH ranging from 6 to 8, before washing the chromatography column with a washing buffer solution containing arginine, and the washing of the chromatography column with the arginine-containing washing buffer solution may be a secondary washing of the chromatography column with a washing buffer solution having a pH ranging from 3 to 5.

Examples of the washing buffer solution to be used in the washing may include a sodium phosphate buffer solution, a sodium acetate buffer solution, a citrate buffer solution, a glycine-HCl buffer solution, a citric acid-sodium phosphate buffer solution, etc. More preferably, the washing buffer solution used in the primary washing may be a sodium phosphate solution having a pH ranging from 6 to 8, and the washing buffer solution used in the secondary washing may be a glycine-HCl solution having a pH ranging from 3 to 5, and NaCl, urea, etc., may be further contained to achieve the desired pH range or ionic strength of the mobile phase.

Figure 2:
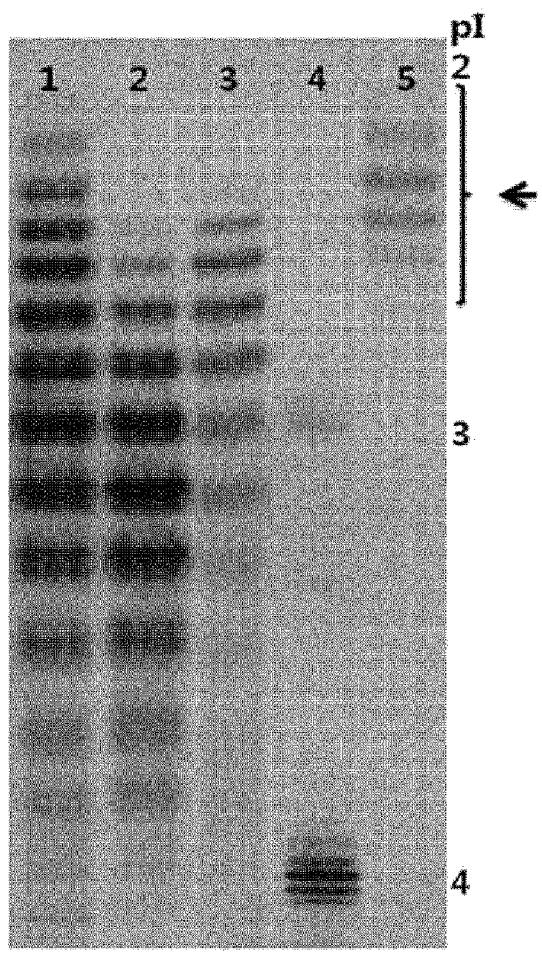
FIG. 2 shows the IEF (Isoelectric focusing) result of anion exchange chromatography, to which a glycine-HCl buffer solution containing arginine was applied.
Figure 3:
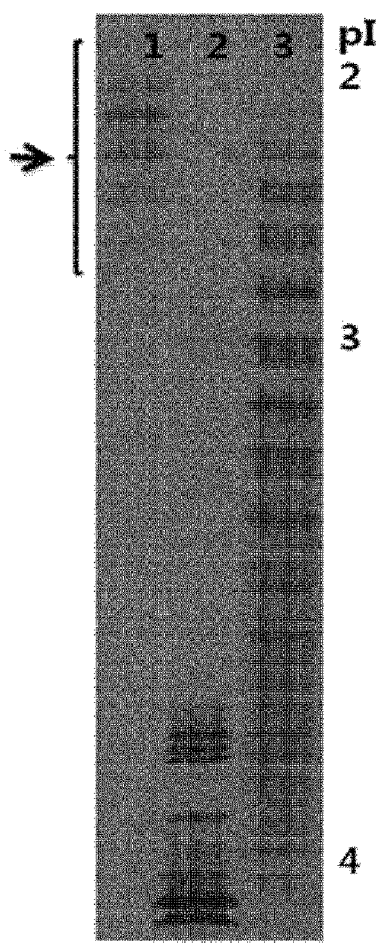
FIG. 3 shows the IEF result of anion exchange chromatography, to which a sodium acetate buffer solution containing arginine was applied.

The arginine-containing washing buffer solution used in the present invention serves an important role of removing darbepoetin alfa with a low sialic acid content. FIG. 2 shows the result of a chromatography performed using a glycine-HCl solution containing arginine as a washing buffer solution, and FIG. 3 shows the result of a chromatography performed using a sodium acetate solution containing arginine as a washing buffer solution. In both cases, it was confirmed that darbepoetin alfa with a high sialic acid content was eluted. That is, when a pH buffer solution containing arginine was applied, high quality darbepoetin alfa having an isoelectric point of from 2 to 3 was shown to be eluted, and in particular, heavily centered around the isoelectric point 2 (arrowed parts on FIGS. 2 and 3).

Figure 4:
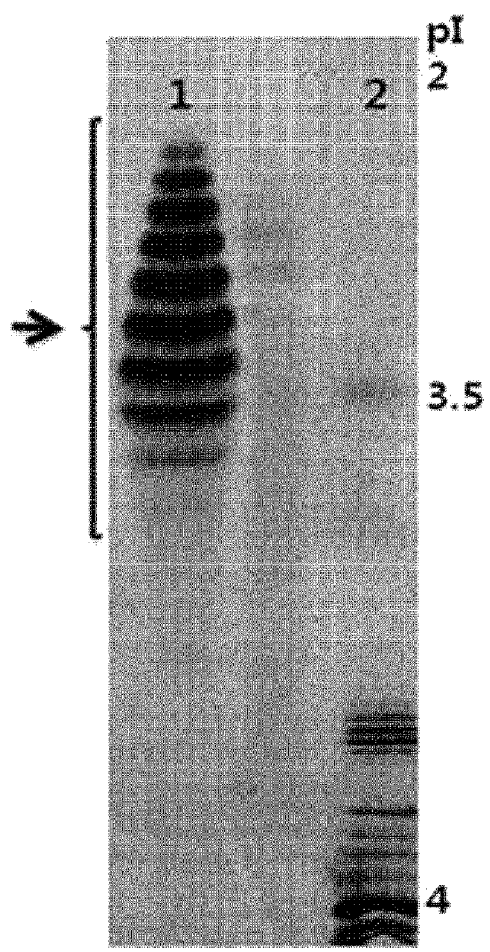
FIG. 4 shows the IEF result of anion exchange chromatography, to which a glycine-HCl buffer solution without arginine was applied.

In contrast, when arginine was not contained in the washing buffer solution while maintaining other conditions to be the same, structural isoforms of darbepoetin alfa with a low sialic acid content were eluted in a large amount around isoelectric point 3 and above isoelectric point 3, thus confirming a significant decrease in the purification effect of the washing buffer solution on structural isoforms of darbepoetin alfa (FIG. 4).

After performing the washing using the arginine-containing washing buffer solution, darbepoetin alfa with a high sialic acid content was eluted by stepwise salt gradient using a buffer solution having a pH ranging from 6 to 8.

In another exemplary embodiment, the present invention provides a purification method for darbepoetin alfa, wherein only the structural isoforms with a high sialic acid content can be selectively separated by further employing gel filtration chromatography. That is, this may be a purification method further including fractionating the anion exchange chromatography eluate obtained above by applying it to gel filtration chromatography.

Gel filtration chromatography is a method of separating proteins according to their size, and may be used for the separation of protein polymers. Examples of the resin to be used in the gel filtration chromatography may include Sephadex™, Sepharose™, Sephacryl™, etc., (GE healthcare), and most preferably, Sephacryl S-100, S-200, and S-300 may be used.

When the anion exchange chromatography eluate, obtained by performing anion chromatography using the washing buffer solution containing arginine, is further subjected to gel-filtration chromatography, darbepoetin alfa with a higher sialic acid content and a purity of 99% or higher may be eluted.

An eluate having a desired isoelectric point may be obtained by sufficiently equilibrating the gel filtration chromatography with a buffer solution; loading the eluate obtained from the anion chromatography using the washing buffer solution containing arginine into the equilibrated gel filtration chromatography column; followed by fractionating the eluate. In the order of fractions, the fraction being eluted earlier may have a higher sialic acid content.

Figure 5:
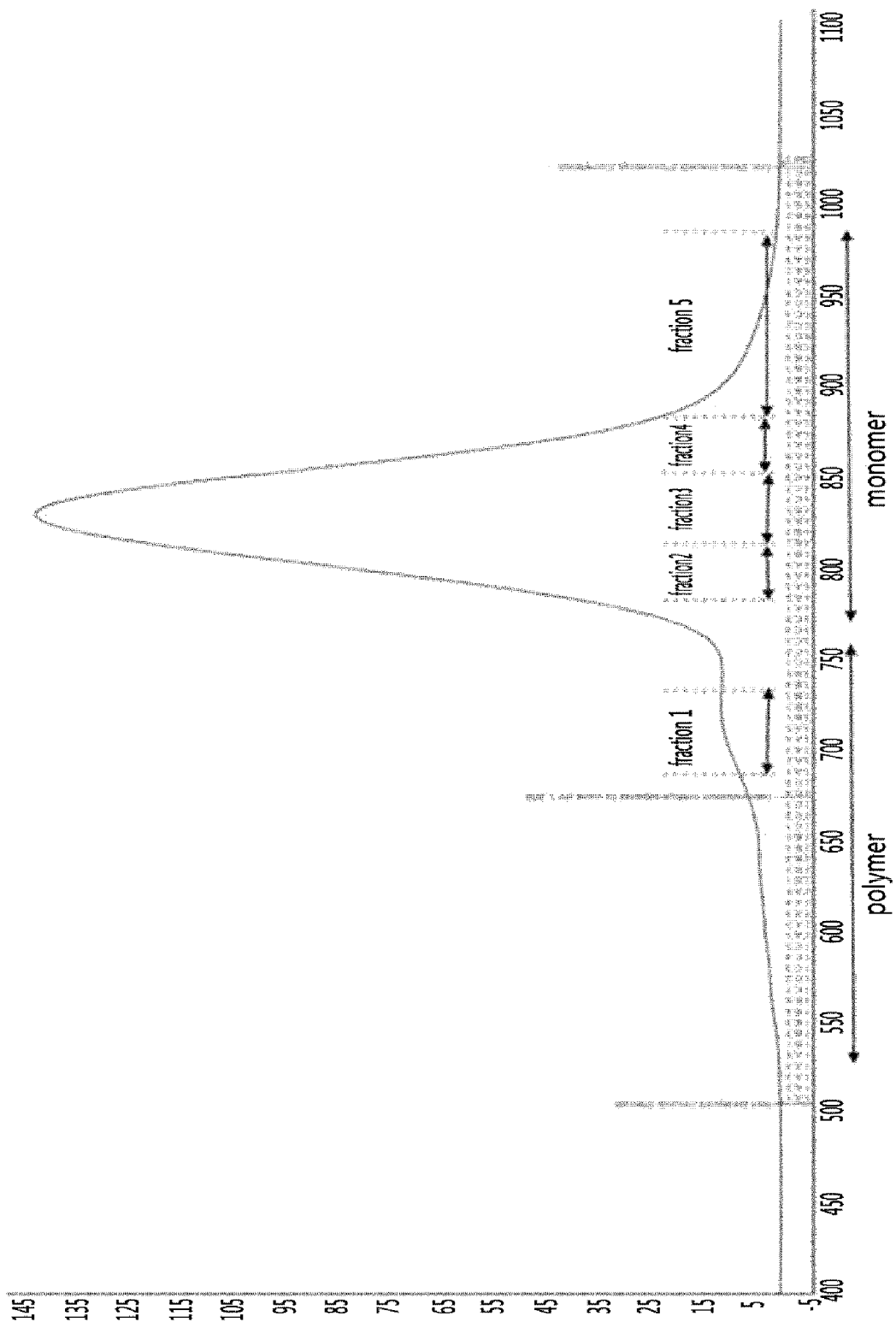
FIG. 5 shows the results of gel filtration chromatography of darbepoetin alfa fractions which were obtained by anion exchange chromatography.
Figure 6:
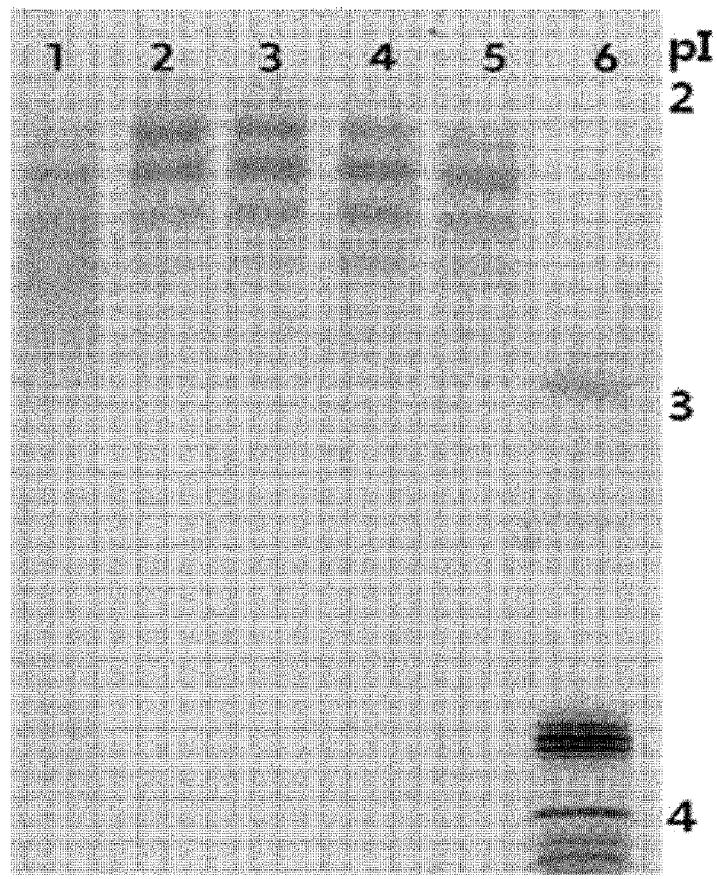
FIG. 6 shows the IEF result showing isoelectric points for each of the fractions in FIG. 5.

In another exemplary embodiment of the present invention, about 1.7 L of Sephacryl S-100 to S-200 (GE Healthcare) resins were filled into an XK-50/90 column (GE Healthcare), and a 20 mM sodium phosphate buffer solution containing 140 mM NaCl (pH 6.2) was sufficiently flowed thereinto to equilibrate the gel filtration column. Then, a solution containing darbepoetin alfa was concentrated, and about 60 mL of the concentrate was flowed into the column at a rate of 7.5 mL/min, and the 20 mM sodium phosphate buffer solution containing 140 mM NaCl (pH 6.2) was sufficiently flowed into the column, thereby fractionating an eluate containing darbepoetin alfa with a high sialic acid content (FIG. 5). It was confirmed that the eluate fractions of darbepoetin alfa had higher sialic acid contents in the order of the fractions (Table 1 and FIG. 6).

In another aspect, the present invention provides a method for purifying darbepoetin alfa including the steps of: (a) eluting a darbepoetin alfa-containing fraction by applying a biological fluid containing darbepoetin alfa to anion exchange chromatography; (b) eluting a darbepoetin alfa-containing fraction by applying the eluate produced in step (a) to hydroxyapatite resin chromatography; (c) binding darbepoetin alfa to an anion exchange chromatography column by loading the eluate produced in step (b) into the anion exchange chromatography column; (d) washing the column treated in step (c) with a washing buffer solution containing arginine; and (e) eluting the darbepoetin alfa, which remains bound to the chromatography column by washing in step (d), from the column.

Each step of the method may be explained in details as shown below.

Step (a) is eluting a darbepoetin alfa-containing fraction by applying a darbepoetin alfa-containing biological fluid to anion exchange chromatography, and preferably, it may be adsorbing the darbepoetin alfa-containing biological fluid to an equilibrated anion exchange chromatography column by adding the darbepoetin alfa-containing biological fluid thereto, washing the column with a washing buffer solution which has a pH ranging from 6 to 8 and contains 10 mM to 100 mM NaCl, and eluting a darbepoetin alfa-containing fraction with an elution buffer solution which has a pH ranging from 6 to 8 and contains 100 mM to 300 mM NaCl.

The anion exchange chromatography and the resin constituting the corresponding column are the same as described above.

Figure 1B:
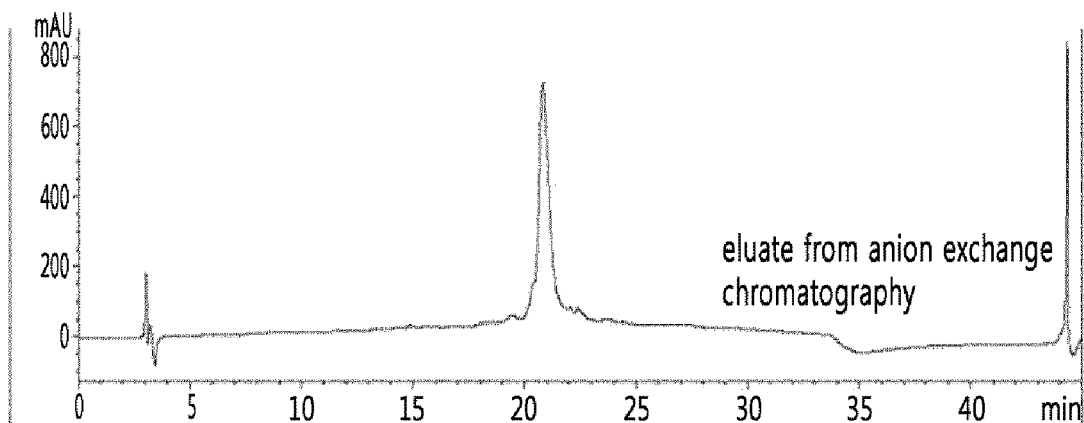

In an exemplary embodiment of the present invention, about 1 L of a culture which was obtained by expressing darbepoetin alfa in CHO cells transfected with a vector containing darbepoetin alfa was diafiltrated by ultrafiltration (MWCO of 10,000) using the 10 mM sodium phosphate buffer solution (pH 7.0) to obtain a biological fluid, which was applied to an XK-50 column filled with a anion exchange (Q fast flow, GE Healthcare) resin equilibrated with a 10 mM sodium phosphate buffer solution (pH 7.0), and again about 2 column volumes (CV) of the 10 mM sodium phosphate buffer solution (pH 7.0) was flowed thereinto to equilibrate the column. Then, the column was washed with a washing buffer solution containing NaCl ranging from 0 mM to 100 mM, and then eluted using an elution buffer solution which has a pH ranging from 6 to 8 and contains 100 mM to 300 mM NaCl. As a result of the anion exchange chromatography, it was confirmed by RP-HPLC that the impurities derived from the biological fluid were removed and the eluate was purified into a solution containing a large amount of darbepoetin alfa (FIG. 1B).

Step (b) is loading the eluate recovered in step (a) into a stationary phase of an equilibrated adsorption chromatography, more preferably, an equilibrated hydroxyapatite resin, washing the resulting resin with a washing buffer solution with a pH ranging from 6 to 8 wherein sodium phosphate, in the range of 0 mM to 100 mM, is contained, thereby obtaining a darbepoetin alfa-containing fraction from the liquid eluted without being adsorbed to the resin during loading and washing.

Examples of the stationary phase of the adsorption chromatography used in the present invention may include silica, alumina, magnesium oxide, and hydroxyapatite, and most preferably hydroxyapatite. As used herein, the term "hydroxyapatite resin chromatography" or "hydroxyapatite chromatography" refers to an adsorption chromatography having a stationary phase filled with a hydroxyapatite resin, and may be interchangeably used with "hydroxyapatite column".

Examples of the buffer solutions used in each of washing and elution steps preferably include a sodium phosphate buffer solution, a potassium phosphate buffer solution, and a Tris buffer solution.

Figure 1C:
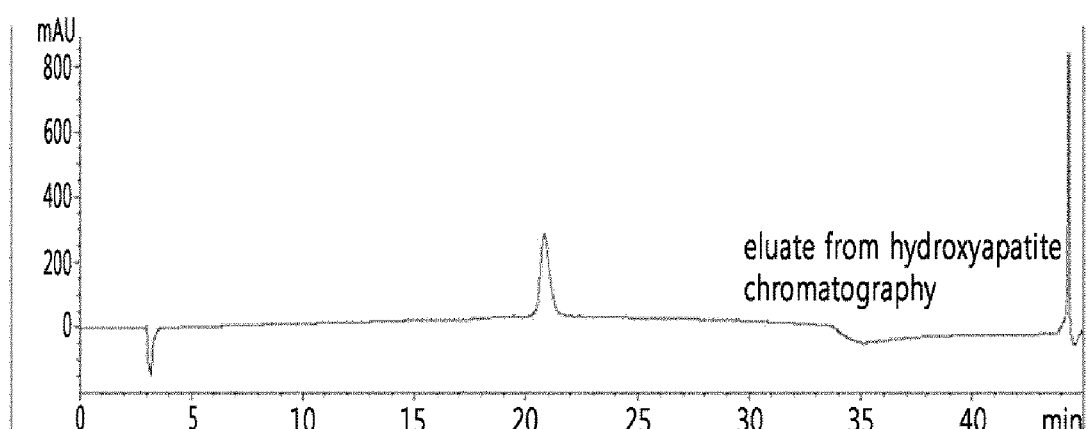

In an exemplary embodiment of the present invention, an anion exchange resin eluate was applied to an XK-50 column filled with a hydroxyapatite resin equilibrated with a 7 mM sodium phosphate buffer solution (pH 7.0), and about three column volumes of the 7 mM sodium phosphate buffer solution (pH 7.0) was flowed thereinto, and thereby darbepoetin alfa with many glycans bound thereto was eluted. As a result of the hydroxyapatite resin chromatography, it was confirmed by RP-HPLC that the impurities derived from the biological fluid were removed and the eluate was purified into a solution containing a large amount of darbepoetin alfa (FIG. 1C).

Mode for Invention

Hereinafter, the present invention will be described in more detail with reference to the following Examples. However, these Examples are for illustrative purposes only, and the invention is not intended to be limited by these Examples.

EXAMPLE 1

Obtaining a Mixture of Darbepoetin Alfa Isoforms having Various Sialic Acid Contents by Anion Exchange Chromatography and Hydroxyapatite Adsorption Chromatography About 1 L of a culture, which was obtained by expressing darbepoetin alfa in CHO cells transfected with a vector containing a nucleotide sequence encoding darbepoetin alfa, was diafiltrated by ultrafiltration (MWCO of 10,000) using the 10 mM sodium phosphate buffer solution (pH 7.0) to obtain a biological fluid. The resultant was sequentially subjected to two columns of anion exchange chromatography and hydroxyapatite adsorption chromatography.

First, the anion exchange chromatography was performed as follows. About 100 mL of an anion exchange (Q fast flow, GE Healthcare) resin was filled into an XK-50 column (GE Healthcare) and a 10 mM sodium phosphate buffer solution (pH 7.0) was flowed thereinto to equilibrate the column. The diafiltrate was flowed in the amount of about 0.1 L to 0.2 L into a Q Sepharose FF column prepared therein at a rate of 15 mL/min, and then about 2 column volumes (CV) of 10 mM sodium phosphate buffer solution (pH 7.0) was again flowed thereinto to equilibrate the column. The column was washed with a washing buffer solution containing 10 mM to 100 mM NaCl and then eluted using an elution buffer solution which has a pH from 6 to 8 and contains 100 mM to 300 mM NaCl.

Second, the eluate, which underwent the anion exchange chromatography, was subjected to hydroxyapatite adsorption chromatography as specified below. About 100 mL of a hydroxyapatite (GE Healthcare) resin was filled into an XK-50 column (GE Healthcare) and a 7 mM sodium phosphate buffer solution (pH 7.0) was flowed thereinto to equilibrate the column. About 0.1 L of diafiltrate was flowed into the hydroxyapatite column prepared therein at a rate of 10 mL/min, and then about 3 column volumes (CV) of 7 mM sodium phosphate buffer solution (pH 7.0) was again flowed thereinto.

In particular, the solutions eluted without being adsorbed to the resin during loading and washing contained darbepoetin alfa with various sialic acid contents, and these solutions were collected and subjected to the subsequent process. After washing, 0.1 M to 0.7 M potassium phosphate buffer solution (pH 7) was flowed into the resin and the fraction(s) containing darbepoetin alfa with low glycans and impurities were removed by elution. The removal of biologically derived impurities and a large amount of darbepoetin alfa in the solutions were confirmed by RP-HPLC (FIG. 1).

EXAMPLE 2

Purification of Darbepoetin Alfa with High Sialic Acid Content by Washing Method Applying Arginine in Anion Exchange Chromatography About 20 mL of a Q Sepharose FF (GE Healthcare) resin was filled into an XK-26 column (GE Healthcare) and a 10 mM sodium phosphate buffer solution (pH 7.0) was sufficiently flowed thereinto to equilibrate the column.

About 0.2 L of the solution containing the darbepoetin alfa obtained in Example 1 was flowed into the column at a rate of 5 mL/min, and then a 10 mM sodium phosphate buffer solution (pH 7.0), which is an equilibrium buffer solution, was flowed thereinto to equilibrate the column. Then, the column was subjected to a primary washing with a 10 mM sodium phosphate buffer solution (pH 7.0) containing 50 mM NaCl, and then subsequently to a secondary washing with a glycine-HCl buffer solution which had a pH from 3 to 5 and contained urea, arginine, and NaCl, thereby washing the fractions containing darbepoetin alfa with a low sialic acid content. The proteins with only a high level of glycosylation and low isoelectric points were eluted using a sodium phosphate buffer solution containing 190 mM NaCl (pH 6.2). The darbepoetin alfa obtained by the washing processes was shown to have high quality by IEF (FIG. 2).

EXAMPLE 3

Measurement of Effect of an Arginine-Containing Washing Solution on Sialic Acid Content The washing method applying arginine in Example 2 was confirmed as playing an important role in purifying darbepoetin alfa with a high sialic acid content.

The solution containing the darbepoetin alfa obtained in Example 1 in the same manner as in Example 2 was adsorbed to a Q Sepharose FF, and about 2 column volumes (CV) of a 10 mM sodium phosphate buffer solution (pH 7.0), which is an equilibrium buffer solution, was flowed into the column to perform the primary washing. However, the secondary washing was performed using a sodium acetate buffer solution with a pH from 3 to 5 or less, instead of the glycine-HCl buffer solution used in Example 2. As a result of the elution, darbepoetin alfa with a high sialic acid content having an isoelectric point of 2~3 or less was confirmed to have been obtained (arrowed part in FIG. 3).

In another aspect, the primary washing and the secondary washing were performed in the same manner as in Example 2, but without arginine. As a result of the elution, even the darbepoetin alfa with a low sialic acid content having an isoelectric point of 2-3 or above was eluted, thus confirming a significant deterioration in its quality (arrowed part in FIG. 4).

In this Example, it was confirmed that arginine is an important factor in obtaining darbepoetin alfa with sialic acid having a low isoelectric point.

EXAMPLE 4

Purification of Darbepoetin Alfa with High Sialic Acid Content by Gel Filtration Chromatography About 1.7 L of Q Sephacryl S-100 to S-200 (GE Healthcare) resins were filled into an XK-50/90 column (GE Healthcare) and a 20 mM sodium phosphate buffer solution containing 140 mM NaCl (pH 6.2) was sufficiently flowed thereinto to equilibrate the column.

The solution containing darbepoetin alfa obtained in Example 2 was concentrated, and about 5 mL of the concentrate was flowed into the column at a rate of 7.5 mL/min, and the 20 mM sodium phosphate buffer solution containing 140 mM NaCl (pH 6.2) was sufficiently flowed into the column, thereby fractionating an eluate containing darbepoetin alfa with a high sialic acid content (FIG. 5). It was confirmed that the eluate fractions of darbepoetin alfa had higher sialic acid contents in the order of the fractions (Table 1 and FIG. 6). The result of Wax-HPLC showing the sialic acid content according to each fraction is shown in Table 1 below.

TABLE 1

| Tetra-sialyated N-Glycan(%) | | | | |
| --- | --- | --- | --- | --- |
| Fraction 1 | Fraction 2 | Fraction 3 | Fraction 4 | Fraction 5 |
| 53.6 | 71.1 | 70.7 | 64.9 | 46.7 |

Summarizing the above results, in the cases of using an anion exchange column, it was confirmed that darbepoetin alfa with a high sialic acid content can be purified by a washing process using an arginine-containing buffer solution. Additionally, as a result of fractionation after further performing gel filtration chromatography thereafter, it was confirmed that darbepoetin alfa with a high sialic acid content and high purity can be purified by the method of the present invention.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method for purifying darbepoetin alfa, comprising:
   (a) binding darbepoetin alfa to an anion exchange chromatography column by loading a mixture comprising darbepoetin alfa having various contents of sialic acid into the anion exchange chromatography column;
   (b) washing the chromatography column with a primary washing buffer solution having a pH ranging 6 to 8, wherein the primary washing buffer solution is a sodium phosphate solution;
   (c) removing darbepoetin alfa having an isoelectric point (pI) less than 2.0 and above 4.0 by washing the chromatography column with a secondary washing buffer solution containing arginine and having a pH ranging 3 to 5, wherein the secondary washing buffer solution is a glycine-HCl solution; and
   (d) eluting the darbepoetin alfa, which remains bound to the chromatography column, from the column, wherein the darbepoetin alfa eluted in step (d) has an isoeletric point ranging from pI 2.0 to 4.0.

2. The method of claim 1, wherein the washing buffer solution containing arginine further comprises at least one selected from the group consisting of NaCl and urea.

3. The method of claim 2, wherein the washing buffer solution comprises NaCl at a concentration ranging from 5 mM to 90 mM.

4. The method of claim 2, wherein the washing buffer solution comprises urea at a concentration ranging from 3 M to 8 M.

5. The method of claim 1, further comprising washing with a washing buffer solution with or without arginine, before or after step (c).

6. The method of claim 1, wherein the biological fluid is an yeast culture, a plant cell culture, or an animal cell culture.

7. The method of claim 1, wherein the anion exchange chromatography column comprises a resin having a functional group which is selected from the group consisting of a quaternary amine (Q), diethylaminoethyl (DEAE), and quaternary aminoethyl (QAE).

8. The method of claim 1, further comprising (e) fractionating the anion exchange chromatography eluate obtained in step (d) by applying it to gel filtration chromatography.

9. A method for purifying darbepoetin alfa, comprising:
   (a) eluting a darbepoetin alfa-containing fraction by applying a biological fluid comprising darbepoetin alfa to anion exchange chromatography;
   (b) eluting a darbepoetin alfa-containing fraction by applying the eluate produced in step (a) to adsorption chromatography;
   (c) binding darbepoetin alfa to an anion exchange chromatography column by loading the eluate produced in step (b) into the anion exchange chromatography column;
   (d) washing the chromatography column with a primary washing buffer solution having a pH ranging 6 to 8, wherein the primary washing buffer is a sodium phosphate solution;
   (e) removing darbepoetin alfa having an isoelectric point (pI) less than 2.0 and above 4.0 by washing the column treated in step (d) with a secondary washing buffer solution containing arginine and having a pH ranging 3 to 5, wherein the secondary washing buffer solution is a glycine-HCl solution; and
   (f) eluting the darbepoetin alfa, which remains bound to the chromatography column by washing in step (e), from the column, wherein the darbepoetin alfa eluted in step (f) has an isoeletric point ranging from pI 2.0 to 4.0.

10. The method of claim 1, wherein the stationary phase of the adsorption chromatography is a hydroxyapatite resin.

11. The method of claim 9, further comprising (g) fractionating the anion exchange chromatography eluate obtained in step (f) by applying it to gel filtration chromatography.

12. The method of claim 9, wherein step (a) comprises adsorbing a darbepoetin alfa-containing biological fluid to an equilibrated anion exchange resin by adding it thereto, washing the resulting resin with a washing buffer solution which has a pH from 6 to 8 and contains 0 mM to 100 mM NaCl, and eluting a darbepoetin alfa-containing fraction with an elution buffer solution which has a pH from 6 to 8 and contains 100 mM to 300 mM NaCl.

13. The method of claim 9, wherein step (b) comprises loading the eluate recovered in step (a) into an equilibrated hydroxyapatite resin, washing the resulting resin with a washing buffer solution which has a pH from 6 to 8 and contains 0 mM to 100 mM sodium phosphate, and obtaining a darbepoetin alfa-containing fraction from the liquid coming out of the resin without being adsorbed thereto during loading and washing.

14. A method for purifying darbepoetin alfa, comprising:
   (a) removing biological impurities from a darbepoetin alfa solution.
   (b) binding darbepoetin alfa in the darbepoetin alfa solution to an anion exchange chromatography column by loading a mixture comprising darbepoetin alfa having various contents of sialic acid into the anion exchange chromatography column;
   (c) washing the chromatography column with a primary washing buffer solution having a pH ranging 6 to 8, wherein the primary washing buffer solution is a sodium phosphate solution;
   (d) removing darbepoetin alfa having an isoelectric point (pI) less than 2.0 and above 4.0 by washing the chromatography column with a secondary washing buffer solution containing arginine and having a pH ranging 3 to 5, wherein the secondary washing buffer solution is a glycine-HCl solution; and
   e) eluting the darbepoetin alfa, which remains bound to the chromatography column, from the column, wherein the darbepoetin alfa eluted has an isoelectric point ranging from pI 2.0 to 4.0.

* * * * *